United States Patent [19]

Tucker et al.

[11] Patent Number: 5,574,196
[45] Date of Patent: Nov. 12, 1996

[54] PROCESS FOR PREPARING ALKANOLS

[75] Inventors: Charles E. Tucker; Diane E. Allen; Charles C. Hobbs, all of Corpus Christi, Tex.

[73] Assignee: Hoechst Celanese Corporation, Somerville, N.J.

[21] Appl. No.: 395,267

[22] Filed: Feb. 28, 1995

[51] Int. Cl.$^6$ .......................... C07C 29/48; C07C 31/125; C07C 35/06; C07C 35/21

[52] U.S. Cl. .......................... 568/838; 568/819; 568/832; 568/910

[58] Field of Search .................................. 568/819, 832, 568/838, 910

[56] References Cited

FOREIGN PATENT DOCUMENTS 272738  8/1964  Australia ........................... 568/832

Primary Examiner—Joseph E. Evans
Attorney, Agent, or Firm—James J. Mullen; Donald R. Cassady

[57] ABSTRACT

A process for preparing tertiary alkanols which comprises the step of oxidizing with ozone a saturated hydrocarbon having a tertiary carbon center in the presence of a carboxylic acid and for a sufficient period of time and at suitable temperature and pressure to form said alkanols.

17 Claims, No Drawings

5,574,196

PROCESS FOR PREPARING ALKANOLS

BACKGROUND OF THE INVENTION

1. Field of the Invention

The present invention is directed to a novel process for preparing alkanols from alkanes which have a tertiary carbon center. These alkanols (sometimes referred to herein as alcohols) have numerous utilities. For example, 1-methylcyclopentanol can be used as an intermediate to prepare 6-chloro-2-hexanone which is a final intermediate in the manufacture of the vasodilator drug pentoxifylline, commonly sold under the trademark Trental.

In the past, such alkanols have been prepared by oxidation procedures which were very inefficient and gave low yields. The desire to provide a new procedure for preparing such alkanols at substantially increased yields was apparent but not accomplished until the present invention.

2. Description of the Prior Art

The following prior art references are disclosed in accordance with the terms of 37 CFR 1.56, 1.93, and 1.97.

U.S. Pat. No. 2,497,349 discloses a process for preparing alicyclic alcohols from various hydrocarbons including methylcyclopentane.

U.S. Pat. No. 2,615,921 discloses as process for the oxidation of napathenic hydrocarbons including methylcyclopentane.

U.S. Pat. No. 3,391,190 discloses a continuous process for oxidizing lower alkanes and cycloalkanes, particularly cyclohexane, to ketones and alcohols.

U.S. Pat. No. 4,588,846 discloses a process for producing a cyclic alcohol (such as cyclopentanol) by catalytic hydration of a cyclic olefin (such as cyclopentene) in a liquid phase.

U.S. Pat. No. 4,661,639 discloses a process for producing a cyclic alcohol (such as cyclohexanol) by catalytic hydration of a cyclic olefin (such as cyclohexene).

U.S. Pat. No. 4,849,550 discloses a method for producing cycloalkanols by the hydration of cycloalkenes (such as methylcyclopentene) with aromatic sulfonic acids as a catalyst.

*Journal of Organic Chemistry.*, 1975, 40, 2141 discloses oxidation with ozone/silica gel at very low temperature but low yields.

*Journal of the American Chemical Society.* 1979 (January 17), 101:2, 502–503 discloses reactions in dry media and the cleavage of carbon-hydrogen single bonds by ozonation.

Russian (Soviet) Patent No. 570588 (Sep. 22, 1977) discloses the production of alicyclic alcohols from the corresponding hydrocarbons using $O_3$-air at 70° C.–140° C., but with very low yields.

All of the above cited prior art and any other references mentioned herein are incorporated herein by reference in their entirety.

SUMMARY OF THE INVENTION

The present invention provides a novel process for preparing tertiary alkanols which comprises the step of oxidizing with ozone a saturated hydrocarbon having a tertiary carbon center in the presence of a carboxylic acid and for a sufficient period of time and at suitable temperature and pressure to form said alkanols.

DETAILED DESCRIPTION OF THE INVENTION

The novel process of the present invention provides for the production of alkanols from alkanes having a tertiary carbon center and in high yields and which has been unobtainable using the prior procedures. This process for preparing tertiary alkanols comprises the step of oxidizing with ozone a saturated hydrocarbon in the presence of a carboxylic acid and for a sufficient period of time and at suitable temperature and pressure to form said alkanols.

The starting materials used in the present invention are saturated hydrocarbons (SH) and particularly those who have five to twelve carbon atoms (i.e. $C_5$–$C_{12}$). These saturated hydrocarbons are selected from the group consisting of (a) cycloalkanes; (b) substituted straight chain alkanes; and (C) bicycloalkanes. Examples of these materials include, without limitation, methylcyclohexane, methylcyclopentane, cis-decahydronaphthalene, transdecahydronaphthalene, and 3-methylpentane. All of the starting materials must have a tertiary carbon atom in order to carry out this novel procedure. All of the starting materials (SH) are also commercially available products.

The conversion of the saturated hydrocarbons (SH) into alkanols is accomplished by reacting the SH with ozone ($O_3$) in the presence of a carboxylic acid (CA), which is critical to the formation of the alkanols in high yields. The carboxylic acid employed has the general formula $RCO_2H$ wherein R is an alkyl group, straight or branched, having from 1 to 8 carbon atoms, i.e. $C_1$–$C_8$. Carboxylic acids (CA) which have been found to be suitable include, without limitation, acetic acid, propionic acid, butyric acid, isobutyric acid, caproic acid, valeric acid, and mixtures thereof. The amount of carboxylic acid employed is that which is sufficient to provide a homogeneous solution with SH acid in which the reaction will take place easily. In general, the molar ratio of SH/CA is about 10:1 to about 1:10. The time required to convert SH to alkanols is from about one minute to about twelve hours.

The quantity of ozone ($O_3$) required is any amount which would facilitate the conversion of SH to the alkanols.

The temperature of the reaction is generally below about 100 ° C., preferably from about 0° C. to about 50° C., more preferably from about 10° C. to about 30° C.

The pressure employed in this reaction is generally atmospheric; however, sub-atmospheric or super-atmospheric pressure can be employed as long as the desired end result is achieved.

As will be seen from the following examples, a combination of time, temperature, concentrations, and acid (CA) provides a novel and efficient process which has heretofore not been obtainable.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

The following procedure was used to prepare 1-methylcyclopentanol (MCPO). Into a three inlet glass flask (500 ml capacity) fitted with a thermometer, reflux condenser, stirrer and sparging tube, there was added 50 ml of isobutyric acid and then 4.2 grams (50 mmol) of methylcyclopentane and it was dissolved therein. At this point, ozone (O₃) was bubbled through the mixture at room temperature (2 SCFH, approximately 3 wt % O₃ in air) and stirring commenced. The reaction was complete after two hours and the reaction mixture diluted with 150 ml of ether to yield a single organic phase. This was then washed one time with 250 ml of saturated NaHCO₃ to yield an organic phase and an aqueous phase which were separated. The organic phase was then washed with sufficient (dilute) KOH to adjust the pH to 8 and thus form an organic phase and an aqueous phase which were separated. The aqueous phases of these washings were then combined, and then added thereto was a sufficient amount of KOH to adjust the pH to 8. The combined aqueous phases were then extracted by use of 150 ml ether (three times). These ether extractions were then combined and the resultant organic phase dried by use of MgSO₄. The MgSO₄ was removed by filtering and the resultant organic phase was concentrated and the product was isolated by distilling (134°–138° C.) under atmospheric pressure. The final product was shown to be MCPO by NMR. There was a 95% conversion and a 99.4% selectivity.

EXAMPLE 2

Into a three inlet glass flask (500 ml capacity) fitted with a thermometer, reflux condenser, stirrer and sparging tube, there was added 75 ml of propanoic acid and then 5.0 grams (59.5 mmol) of methylcyclopentane and it was dissolved therein. At this point, ozone (O3) was bubbled through the mixture at room temperature (2 SCFH, approximately 3 wt % O₃ in air) and stirring commenced. The reaction was complete after 5½ hours and the reaction mixture diluted with 200 ml of ether to yield a single organic phase. This was then washed four times with 250 ml of saturated NaHCO₃ to yield an organic phase and an aqueous phase which were separated. The organic phase was then washed with sufficient (dilute) KOH to adjust the pH to 8 and thus form an organic phase and an aqueous phase which were separated. The aqueous phases of these washings were then combined, and then added thereto was a sufficient amount of KOH to adjust the pH to 8. The combined aqueous phases were then extracted by use of 200 ml ether (two times). These ether extractions were then combined and the resultant organic phase dried by use of MgSO₄. The MgSO₄ was removed by filtering and the resultant organic phase was concentrated and the product was isolated by distilling (135°–139° C.) under atmospheric pressure. The final product was shown to be 1-methylcyclopentanol (MCPO) by NMR. There was a 70.9% yield.

EXAMPLE 3

The following procedure was used to prepare 3-methyl-3-pentanol (MPO). Into a three inlet glass flask (500 ml capacity) fitted with a thermometer, reflux condenser, stirrer and sparging tube, there was added 40 ml of isobutyric acid and then 4.3 grams (50 mmol) of 3-methylpentane and it was dissolved therein. At this point, ozone (O₃) was bubbled through the mixture at room temperature (2 SCFH, approximately 3 wt % O₃ in air) and stirring commenced. The reaction was complete after ten hours and the reaction mixture diluted with 150 ml of ether to yield a single organic phase. This was then washed one time with 250 ml of saturated NaHCO₃ to yield an organic phase and an aqueous phase which were separated. The organic phase was then washed with sufficient (dilute) KOH to adjust the pH to 8 and thus form an organic phase and an aqueous phase which were separated. The aqueous phases of these washings were then combined, and then added thereto was a sufficient amount of KOH to adjust the pH to 8. The combined aqueous phases were then extracted by use of 150 ml ether (three times). These ether extractions were then combined and the resultant organic phase dried by use of MgSO₄. The MgSO₄ was removed by filtering and the resultant organic phase was concentrated and the product was isolated by distilling under atmospheric pressure. The final product was shown to be MPO by NMR. There was a 61.8% yield.

EXAMPLE 4

Into a three inlet glass flask (500 ml capacity) fitted with a thermometer, reflux condenser, stirrer and sparging tube, there was added 40 ml of butyric acid and then 4.2 grams (50 mmol) of methylcyclopentane and it was dissolved therein. At this point, ozone (O₃) was bubbled through the mixture at room temperature (2 SCFH, approximately 3 wt % O₃ in air) and stirring commenced. The reaction was complete after three hours and the reaction mixture diluted with 150 ml of ether to yield a single organic phase. This was then washed one time with 250 ml of saturated NaHCO₃ to yield an organic phase and an aqueous phase which were separated. The organic phase was then washed with sufficient (dilute) KOH to adjust the pH to 8 and thus form an organic phase and an aqueous phase which were separated. The aqueous phases of these washings were then combined, and then added thereto was a sufficient amount of KOH to adjust the pH to 8. The combined aqueous phases were then extracted by use of 150 ml ether (three times). These ether extractions were then combined and the resultant organic phase dried by use of MgSO₄. The MgSO₄ was removed by filtering and the resultant organic phase was concentrated and the product was isolated by distilling (135°–139° C.) under atmospheric pressure. The final product was shown to be 1-methylcyclopentanol (MCPO) by NMR. There was an 87.8% yield.

EXAMPLE 5

The following procedure was used to prepare 1-methylcyclopentanol (MCPO). Into a three inlet glass flask (500 ml capacity) fitted with a thermometer, reflux condenser, stirrer and sparging tube, there was added 40 ml of valeric acid and then 4.2 grams (50 mmol) of methylcyclopentane and it was dissolved therein. At this point, ozone (O₃) was bubbled through the mixture at room temperature (2 SCFH, approximately 3 wt % O₃ in air) and stirring commenced. The reaction was complete after three hours and the reaction mixture diluted with 150 ml of ether to yield a single organic phase. This was then washed one time with 250 ml of saturated NaHCO₃ to yield an organic phase and an aqueous phase which were separated. The organic phase was then washed with sufficient dilute KOH to adjust the pH to 8 and thus form an organic phase and an aqueous phase which were separated. The aqueous phases of these washings were then combined, and then added thereto was a sufficient amount of KOH to adjust the pH to 8. The combined aqueous phases were then extracted by use of 150 ml ether (three times). These ether extractions were then combined and the resultant organic phase dried by use of MgSO₄. The MgSO₄ was removed by filtering and the resultant organic phase was concentrated and the product was isolated by distilling (133°–136° C.) under atmospheric pressure. The final product was shown to be MCPO by NMR. There was a 75.4% yield.

EXAMPLE 6

The following procedure was used to prepare 1-methylcyclopentanol (MCPO). Into a three inlet glass flask (500 ml capacity) fitted with a thermometer, reflux condenser, stirrer and sparging tube, there was added 40 ml of valeric acid and then 4.2 grams (50 mmol) of methylcyclopentane and it was dissolved therein. At this point, ozone ($O_3$) was bubbled through the mixture at room temperature (2 SCFH, approximately 3 wt % $O_3$ in air) and stirring commenced. The reaction was complete after 4-¾ hours and the reaction mixture diluted with 150 ml of ether to yield a single organic phase. This was then washed one time with 250 ml of saturated $NaHCO_3$ to yield an organic phase and an aqueous phase which were separated. The organic phase was then washed with sufficient (dilute) KOH to adjust the pH to 8 and thus form an organic phase and an aqueous phase which were separated. The aqueous phases of these washings were then combined, and then added thereto a sufficient amount of KOH to adjust the pH to 8. The combined aqueous phases were then extracted by use of 150 ml ether (three times). These ether extractions were then combined and the resultant organic phase dried by use of $MgSO_4$. The $MgSO_4$ was removed by filtering and the resultant organic phase was concentrated and the product was isolated by distilling (124°–128° C.) under atmospheric pressure. The final product was shown to be MCPO by NMR. There was a 77.6% yield.

EXAMPLE 7

The following procedure was used to prepare 9-hydroxy-decalin. Into a three inlet glass flask (500 ml capacity) fitted with a thermometer, reflux condenser, stirrer and sparging tube, there was added 40 ml of isobutyric acid and then 6.9 grams (50 mmol) of cis-decalin and it was dissolved therein. At this point, ozone ($O_3$) was bubbled through the mixture at room temperature (2 SCFH, approximately 3 wt % $O_3$ in air) and stirring commenced. The reaction was complete after 7-½ hours and the reaction mixture diluted with 150 ml of ether to yield a single organic phase. This was then washed one time with 250 ml of saturated $NaHCO_3$ to yield an organic phase and an aqueous phase which were separated. The organic phase was then washed with sufficient dilute KOH to adjust the pH to 8 and thus form an organic phase and an aqueous phase which were separated. The aqueous phases of these washings were then combined, and then added thereto was a sufficient amount of KOH to adjust the pH to 8. The combined aqueous phases were then extracted by use of 150 ml ether (three times). These ether extractions were then combined and the resultant organic phase dried by use of $MgSO_4$. The $MgSO_4$ was removed by filtering and the resultant organic phase was concentrated by distilling under atmospheric pressure. The concentrate was diluted with 50 ml hexane and then filtered through twenty grams of silica gel. The silica gel was washed with 250 ml hexane. The hexane solutions were distilled to obtain the 9-hydroxydecalin. There was a 73.1% yield.

EXAMPLE 8 (COMPARABLE)

The following procedure was used to prepare 1-methylcyclopentanol (MCPO) without the use of a carboxylic acid. Into a three inlet glass flask (500 ml capacity) fitted with a thermometer, reflux condenser, stirrer and sparging tube, there was added 4.2 grams (50 mmol) of methylcyclopentane (MCP). At this point, ozone ($O_3$) was contacted with the MCP at room temperature (2 SCFH, approximately 3 wt % $O_3$ in air) and stirring commenced. The reaction was complete after eight hours and the reaction mixture diluted with 150 ml of ether to yield a single organic phase. This was then washed one time with 250 ml of water to yield an organic phase and an aqueous phase which were separated. The aqueous phase was then extracted by use of 150 ml ether (three times). These ether extractions were then combined and the resultant organic phase dried by use of $MgSO_4$. The $MgSO_4$ was removed by filtering and the resultant organic phase was concentrated and the product isolated by distilling (134°–138° C.) under atmospheric pressure. The final material was shown to be MCPO by NMR. There was a 10% conversion and a 6% selectivity; the yield of MCPO was 5%. This is quite a striking contrast to those results obtained in Example 1 where isobutyric acid was used.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing substantially only tertiary alkanols or cycloalkanols which comprises the step of oxidizing with ozone a saturated hydrocarbon having a tertiary carbon center in the presence of a carboxylic acid and for a sufficient period of time and at suitable temperature and pressure to form substantially only said alkanols, with the proviso that said carboxylic acid is initially present in an amount which provides a homogeneous solution with said hydrocarbon and functions both as a catalyst and as a solvent.

2. The process as set forth in claim 1 wherein the saturated hydrocarbon contains from five to twelve carbon atoms.

3. The process as set forth in claim 1 wherein the saturated hydrocarbon is selected from the group consisting of (a) cycloalkanes; (b) branched chain alkanes; and (c) bicycloalkanes.

4. The process as set forth in claim 1 wherein the carboxylic acid used has the formula $RCO_2H$ where R is alkyl $C_1$–$C_2$.

5. The process as set forth in claim 1 wherein the carboxylic acid is isobutyric acid.

6. The precess as set forth in claim 1 wherein the carboxylic acid is aceticacid.

7. The process as set forth in claim 1 wherein the carboxylic acid is a mixture of acetic acid and isobutyric acid.

8. The process as set forth in claim 1 wherein the temperature is from about 0° C. to about 50° C.

9. The process as set forth in claim 1 wherein the temperature is from about 10° C. to about 30° C.

10. A process for preparing substantially only 1-methylcyclopentanol which comprises the step of oxidizing methylcyclopentane with ozone in the presence of a carboxylic acid and for a sufficient period of time and at a suitable temperature to form substantially only 1-methylcyclopentanol, with the proviso that said carboxylic acid is initially present in an mount which provides a homogeneous solution with said methylcyclopentane and functions both as a catalyst and as a solvent.

11. The process as set forth in claim 10, wherein the carboxylic acid used has the formula $RCO_2H$ where R is alkyl $C_1$–$C_2$.

12. The process as set forth in claim 10, wherein the carboxylic acid is isobutyric acid.

13. The process as set forth in claim 10, wherein the carboxylic acid is acetic acid.

14. The process as set forth in claim 10, wherein the temperature is from about 0° C. to about 50° C.

15. The process as set forth in claim 10, wherein the carboxylic acid is a mixture of acetic acid and isobutyric acid.

16. The process as set forth in claim 1, wherein the carboxylic acid is pivalic acid.

17. The process as set forth in claim 10, wherein the carboxylic acid is pivalic acid.

* * * * *